(12) United States Patent
Duong et al.

(10) Patent No.: US 6,734,193 B1
(45) Date of Patent: May 11, 2004

(54) (1,2,3,4-TETRAHYDROQUINOLIN-8-YL)-HEPTATRIENOIC ACID DERIVATIVES HAVING SERUM GLUCOSE REDUCING ACTIVITY

(75) Inventors: Tien Duong, Irvine, CA (US); Richard L. Beard, Newport Beach, CA (US); Roshantha A. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/452,956

(22) Filed: Jun. 3, 2003

(51) Int. Cl.$^7$ .................. A61K 31/47; C07D 215/14; C07D 215/02; A61P 3/10

(52) U.S. Cl. .................. 514/311; 514/277; 546/166; 546/165; 546/174

(58) Field of Search .................. 546/166, 165, 546/174; 514/311, 277

(56) References Cited

U.S. PATENT DOCUMENTS

| | | | |
|---|---|---|---|
| 4,810,804 A | 3/1989 | Chandraratna | |
| 5,278,318 A | 1/1994 | Chandraratna | |
| 5,399,561 A | 3/1995 | Chandraratna | |
| 5,455,265 A | 10/1995 | Chandraratna | |
| 5,498,795 A | 3/1996 | Song et al. | |
| 5,556,996 A | 9/1996 | Beard et al. | |
| 5,602,130 A | 2/1997 | Chandraratna | |
| 5,616,712 A | 4/1997 | Teng et al. | |
| 5,672,710 A | 9/1997 | Beard et al. | |
| 5,677,323 A | 10/1997 | Chandraratna | |
| 5,721,103 A | 2/1998 | Boehm et al. | |
| 5,739,338 A | 4/1998 | Beard et al. | |
| 5,780,647 A | 7/1998 | Vuligonda et al. | |
| 5,801,253 A | 9/1998 | Klaus et al. | |
| 5,977,125 A | * 11/1999 | Hibi et al. .................. | 514/277 |
| 6,048,873 A | 4/2000 | Vasudevan et al. | |
| 6,114,533 A | 9/2000 | Vuligonda et al. | |
| 6,124,455 A | 9/2000 | Teng et al. | |
| 6,127,382 A | 10/2000 | Beard et al. | |
| 6,147,224 A | 11/2000 | Vuligonda et al. | |
| 6,291,677 B1 | 9/2001 | Vasudevan et al. | |
| 6,326,397 B1 | 12/2001 | Bollag et al. | |
| 6,344,463 B1 | 2/2002 | Chandraratna | |
| 6,469,028 B1 | 10/2002 | Klein et al. | |
| 6,495,552 B2 | 12/2002 | Vasudevan et al. | |

FOREIGN PATENT DOCUMENTS

| | | |
|---|---|---|
| WO | WO-93-11755 | 6/1993 |
| WO | WO-97-12853 | 4/1997 |
| WO | WO-01-19770 | 3/2001 |

OTHER PUBLICATIONS

Mangelsdorf et al. The Retinoid Receptors In: The Retinoids pp. 319–349 (1994).

Dawson et al. Chemistry and Biology of Synthetic Retinoids pp. 324–356 (1990).

Mukherjee et al. R.A. Sensitization of Diabetic and Obese Mice to Insulin by Retinoik X Receptor Agonists. *Nature.* vol. 386 pp. 407–410 (1997).

Heyman et al. 9–Cos Retinoic Acid Is a High Affinity Ligand for the Retinoid X Receptor. *Cell.* vol. 68 pp. 397–406 (1992).

Allegretto et al Trans–activation Properties of Retinoic Acid and Retinoid X Receptors in Mammalian Cells and Yeast. *J. Biol. Chem.* vol. 268 pp. 26625–26633.

Cheng et al. Relationship Between the Inhibition Constant (K1) and the Concentration of Inhibitor Which Causes 50 per cent Inhibition (I50) of an Enzymatic Reaction. *Biological Pharmacology.* vol. 22 pp. 3099–3108.

Feigner et al. Cationic Lipsome–Mediated Transfection. *Focus.* vol. 11 No. 2 pp. 21–24 (1989).

Corey et al. Condensation of an Allylic Phosphate Ylide. Journal of Organic Chemistry vol. 39 p. 821 (1974).

\* cited by examiner

*Primary Examiner*—Evelyn M. Huang
(74) *Attorney, Agent, or Firm*—Gabor L. Szekeres; Robert J. Baran; Martin A. Voet

(57) ABSTRACT

Compounds of the formula

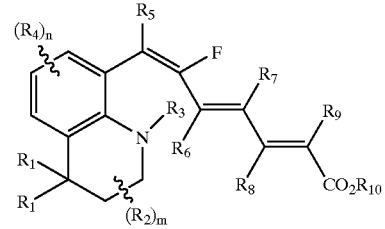

where the variables have the meaning defined in the specification are capable of reducing serum glucose levels in diabetic mammals without the undesirable side effects of reducing serum thyroxine levels and transiently increasing triglyceride levels.

25 Claims, No Drawings

(1,2,3,4-TETRAHYDROQUINOLIN-8-YL)-HEPTATRIENOIC ACID DERIVATIVES HAVING SERUM GLUCOSE REDUCING ACTIVITY

BACKGROUND OF THE INVENTION

Field of Invention

The present invention relates to compounds that have the property of reducing serum glucose and serum triglyceride levels in diabetic mammals without the undesirable properties of reducing serum thyroxine levels and transiently raising triglyceride levels. More particularly, the present invention relates to 5,6,7,8-tetrahydronaphthalen-2-yl 2,6-difluoroheptatrienoic acid derivatives having the above-noted biological property.

Compounds that have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property.

For a general overview of the retinoid receptors see Mangelsdorf et al. (1994) The Retinoid Receptors In: The Retinoids, edited by Sporn et al. p 319–349. Raven Press, Ltd., New York. For another general overview see Dawson and William H. Okamura, Chemistry and Biology of Synthetic Retinoids, published by CRC Press Inc., 1990, pages 324–356. U.S. Pat. Nos. 6,495,552; 6,291,677; 6,344,463; 6,048,873; 6,124,455; 6,147,224; 5,672,710; 5,677,323; 5,739,338; 5,556,996; 5,602,130; 5,616,712; 5,278,318; 5,399,561; 5,498,755; 4,810,804; 5,739,338, 5,780,647, 6,127,382 and 6,469,028 disclose retinoid compounds which include a tetrahydroquinoline or dihydroquinoline nucleus. The following further patents are of interest as general background to the present invention: U.S. Pat. Nos. 5,721,103; 5,801,253; 6,326,397; PCT Publications WO 97/12853 and WO 01/19770.

Relatively recently it has become known that certain retinoid compounds are capable of reducing serum glucose levels in diabetic mammals. Mukhedjee, R.; Davies, P. J.; Crombie, D. L. Bishoff, E. D.; Cesario, R. M.; Jow Hamann, L. G.; Boehm, M. F.; Mondon, C. E.; Nadzan, A. M.; Paterniti, J. R. Jr.; Heyman, R. A. Sensitization of Diabetic and Obese Mice to Insulin by Retinoid X Receptor Agonists. Nature 1997, 386 (6623), 407–410. The compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid, described in U.S. Pat. No. 6,114,533, has this property. A disadvantage of the prior art retinoid compounds that reduce serum glucose levels is that their administration usually also results in the pharmacologically undesirable reduction of serum thyroxine levels and a transient increase in serum triglyceride levels. The present invention is directed to novel compounds which do not have these undesirable side effects.

SUMMARY OF THE INVENTION

The present invention relates to compounds of Formula 1

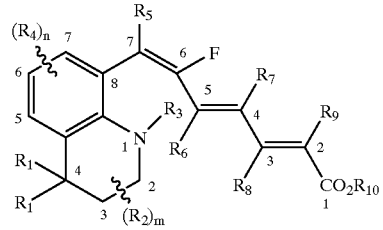

Formula 1 where m is an integer having the values of 0 to 4;

n is an integer having the values of 0 to 3;

$R_1$ is independently H, or alkyl of 1 to 6 carbons;

$R_2$ is independently H, alkyl of 1 to 6 carbons, F, Cl, Br or I;

$R_3$ is alkyl of 1 to 6 carbons;

$R_4$ is independently H, alkyl of 1 to 6 carbons, F, Cl, Br or I;

$R_5$ is alkyl of 1 to 6 carbons;

$R_6$, $R_7$, $R_8$ and $R_9$ are independently, H, alkyl of 1 to 3 carbons, Cl or F;

$R_{10}$ is is H, alkyl of 1 to 6 carbons, $OCH_2OR_{11}$ or $OCH_2OCOR_{11}$ where $R_{11}$ is alkyl of 1 to 3 carbons, or a pharmaceutically acceptable salt of said compound.

The present invention also relates to pharmaceutical compositions incorporating the compounds of Formula 1 and to methods of treatment of diabetic mammals with pharmaceutical compositions containing one or more compounds of Formula 1 to reduce serum glucose levels in said mammals.

The present invention also relates to the methods of using the compounds of the invention to treat diseases and conditions which are responsive to treatment by retinoids.

DETAILED DESCRIPTION OF THE INVENTION

General Embodiments and Synthetic Methodology
Definitions

The term alkyl refers to and covers any and all groups which are known as normal alkyl and branched-chain alkyl.

A pharmaceutically acceptable salt may be prepared for any compound in this invention having a fimctionality capable of forming a salt, for example an acid functionality. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The compounds of the present invention include olephinic double bonds about which trans and cis (E and Z) stereoisomerism can exist. The compounds of the present invention have the specific orientations of substituents relative to the double bonds as is indicated in the name of the respective compound, and/or by specific showing in the structural formula of the orientation of the substituents relative to the respective double bonds. Some of the compounds of the present invention may contain one or more chiral centers and therefore may exist in enantiomeric and diastereomeric forms. The scope of the present invention is intended to cover the trans and cis (E and Z) isomers as specifically shown and/or named, as well as pure enantiomers (optical isomers), diastereomers, mixtures of diastereomers and racemic mixtures of enantiomers.

Reaction Scheme 1 discloses a presently preferred synthetic route to compounds of the invention. Although this synthetic route is general, the cis and/or trans isomerism of the compounds of the invention is indicated properly, the non-aromatic portion of the tetrahydroquinoline condensed ring system is indicated to have no $R_2$ substituent (m is zero; or stated alternatively $R_2$ is hydrogen), and the variables $R_6$, $R_7$ and $R_9$ are hydrogen (H), as in the preferred embodiments. However, based on the present disclosure and general knowledge in the art those having ordinary skill in synthetic methodology can readily modify the herein described reactions to obtain all compounds within the scope of Formula 1.

Referring now to Reaction Scheme 1 the starting material is an aniline derivative of Formula 2 that is already substituted with the $R_4$ groups. The substitituted anilines of Formula 2 are either available commercially, or can be prepared in accordance with the chemical scientific and patent literature, or by such modifications of known synthetic procedures that are readily apparent to those skilled in the art.

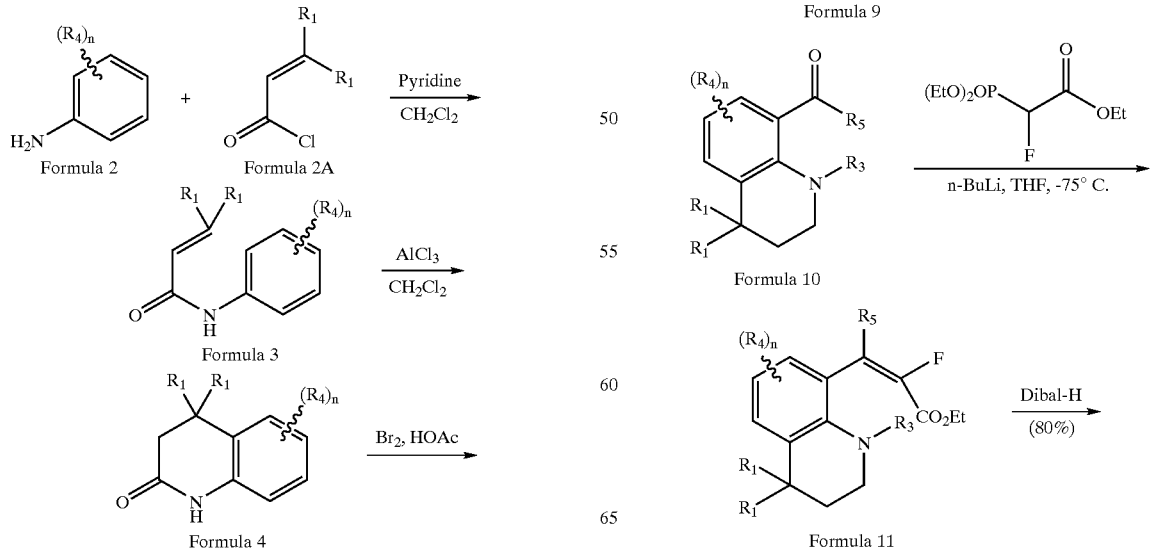

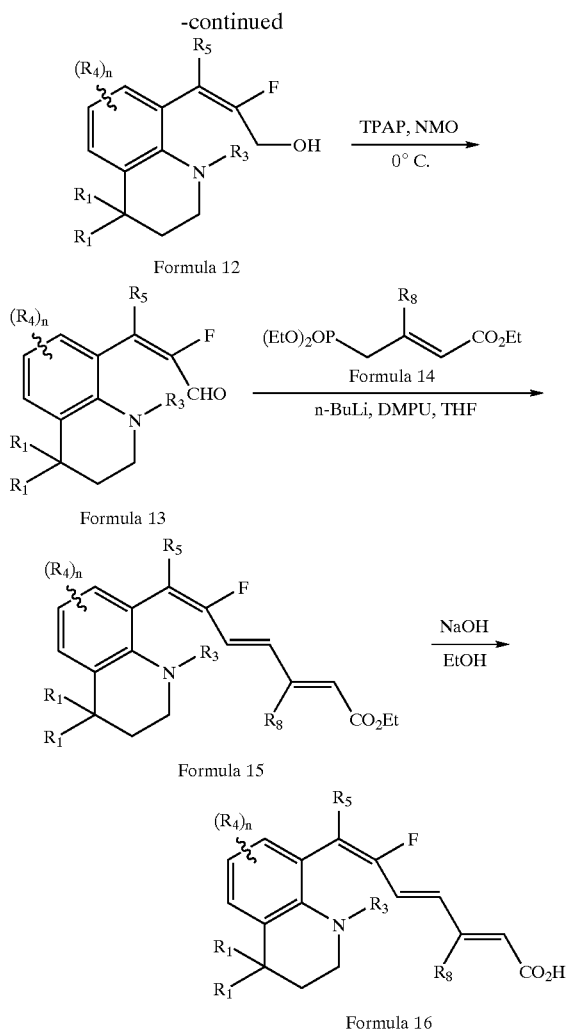

Formula 12

Formula 13

Formula 15

Formula 16

An example for a compound in accordance with Formula 2 is 4-iso-propylaniline that serves as the starting material for the presently preferred compounds of the invention. The aniline derivative of Formula 2 is reacted with an acryloyl chloride derivative of Formula 2A in a basic solvent, such as pyridine, to provide the phenyl amide derivative of the acryloic acid of Formula 3. An example of the acryloyl chloride derivative of Formula 2A that is used for the synthesis of the presently preferred compounds of the invention is commercially available 3,3-dimethylacryloyl chloride. The acryloic acid amide derivative of Formula 3 is cyclized under Friedel Crafts conditions to provide the 1,2,3,4-tetrahydro-quinolin-2-one derivative of Formula 4. The 1,2,3,4-tetrahydro-quinolin-2-one derivative of Formula 4 is reacted with bromine in acetic acid to provide the 8-bromo-1,2,3,4-tetrahydro-quinoline-2-one derivative of Formula 5. The numbering of the quinoline ring system and of the heptatrienoic acid moiety that is attached to it in the 8 position of the quinoline nucleus in the compounds of the invention, is shown in Formula 1. The endocyclic oxo function of the 8-bromo-1,2,3,4-tetrahydro-quinoline-2-one derivative of Formula 5 is reduced by treatment with borane-methyl sulfide to give the 8-bromo-1,2,3,4-tetrahydro-quinoline derivative of Formula 6. An alkyl group, designated $R_3$, where $R_3$ is defined as in connection with Formula 1, is introduced to the nitrogen of the quinoline nucleus by treatment of the compound of Formula 6 with an alkylating agent, such as $R_3$-I, in the presence of base, to give the 1-alkyl-8-bromo1,2,3,4-tetrahydro-quinoline compound of Formula 7. The 1-alkyl-8-bromo1,2,3,4-tetrahydro-quinoline compound of Formula 7 is reacted with dimethylformamide (DMF) in the presence of strong base, such as n-butyl lithium to give a 1-alkyl-1,2,3,4-tetrahydro-quinoline-8-carbaldehyde of Formula 8. The carbaldehyde of Formula 8 is reacted with a Grignard reagent of the formula $R_5MgBr$, where $R_5$ is defined as in connection with Formula 1, to provide a (1-alkyl-1,2,3,4-tetrahydro-quinoline-8-yl)-alkan-1-ol of Formula 9.

The (1-alkyl-1,2,3,4-tetrahydro-quinoline-8-yl)-alkan-1-ol of Formula 9 is oxidized to the ketone level by treatment with tetrapropylammonium perruthenate (TPAP) in the presence of 4-methylmorpholine N-oxide (NMO) and molecular sieves to provide a (1-alkyl-1,2,3,4-tetrahydro-quinoline-8-yl)-alkan-1-one of Formula 10. The (1-alkyl-1,2,3,4-tetrahydro-quinoline-8-yl)-alkan-1-one of Formula 10 is subjected to a Horner Emmons reaction with the reagent triethyl-2-fluoro-2-phosphonoacetate to give a (1-alkyl-1,2,3,4-tetrahydro-quinoline-8-yl)-fluoroalkenoic acid ethyl ester derivative of Formula 11. The reagent triethyl-2-fluoro-2-phosphonoacetate is commercially available (Aldrich Chemical Company). As is well known in the art, the Horner Emmons reaction is conducted at cold temperatures (−75° C.) and in the presence of strong base (n-butyl lithium). The carboxylic acid ester function of (1-alkyl-1,2,3,4-tetrahydro-quinoline-8-yl)-fluoroalkeno acid ethyl ester derivative of Formula 11 is reduced with di-iso-butylaluminum hydride (DIBAL-H) to the primary alcohol level (Formula 12), and the primary alcohol is oxidized with tetrapropylammonium perruthenate (TPAP) in the presence of 4-methylmorpholine N-oxide (NMO) and molecular sieves to provide a (1-alkyl-1,2,3,4-tetrahydro-quinoline-8-yl)-fluoroalken-al of Formula 13.

The aldehyde of Formula 13 is subjected to another Horner Emmons reaction, this time with the reagent of Formula 14 where $R_8$ is defined as in connection with Formula 1. An example for the reagent of Formula 14 that is used for the synthesis of the presently preferred compounds of the invention is ethyl 4-(diethoxyphosphoryl)-3-methyl-but-2-enoate. Ethyl 4-(diethoxyphosphoryl)-3-methylbut-2-enoate can be obtained in accordance with the procedure described in Journal of Organic Chemistry 1974, 39, 821, incorporated herein by reference. Other examples of the reagent of Formula 14 can be prepared by such modifications of this reference or of other known synthetic procedures that are readily apparent to those skilled in the art. The product obtained in this second Horner Emmons reaction is a (1-alkyl-1,2,3,4-tetrahydro-quinoline-8-yl)-fluorohepta-trienoic acid ethyl ester derivative of Formula 15 that is within the scope of the invention and of Formula 1. The ester portion of the compounds of Formula 15 can be saponified to provide a (1-alkyl-1,2,3,4-tetrahydro-quinoline-8-yl)-fluorohepta-trienoic acids of Formula 16, as the free acid, or a pharmaceutically acceptable salts thereof. The compounds of Formula 16 are also within the scope of the invention and of Formula 1.

Specific Embodiments of the Compounds of the Invention

Referring now to Formula 1, in the preferred compounds of the invention the variable $R_1$ represents alkyl groups of 1 to 3 carbons, and even more preferably methyl. Still more preferably the 1,2,3,4-tetrahydroquinoline group is substituted in the 2 position by geminal dimethyl groups, and still further substitution of the non-aromatic portion by additional $R_2$ groups is presently not preferred. The $R_3$ group of the preferred compounds is alkyl of 1 to 3 carbons.

$R_4$ of the preferred compounds is alkyl of 1 to 4 carbons, preferably branch-chained, and even more preferably isopropyl. Preferably there is only one $R_4$ substituent (n=1). $R_5$ is preferably alkyl of 1 to 3 carbons, and $R_8$ is preferably methyl. $R_6$, $R_7$ and $R_9$ preferably are hydrogen (H). $R_{10}$ is preferred as H, or alkyl of 1 to 3 carbons or methoxymethyl, or as a pharmaceutically acceptable salt of the carboxylic acid. Still more preferably $R_{10}$ is H (or a salt of the carboxylic acid) or ethyl.

The synthesis of the presently most preferred compounds of the invention is shown in Reaction Scheme 2 and a detailed description of the experimental procedures for synthesizing these most preferred exemplary compounds is also provided below.

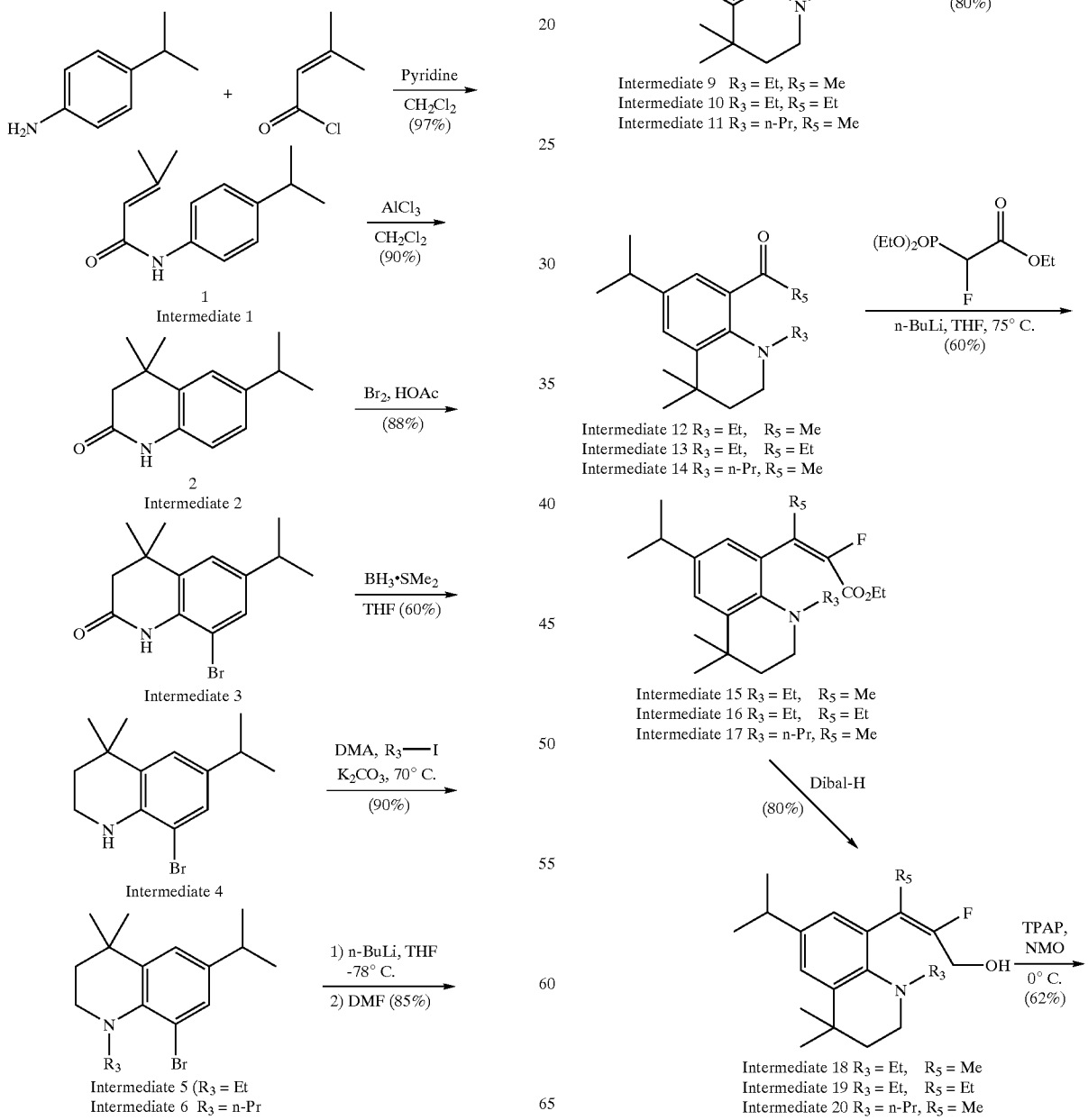

-continued

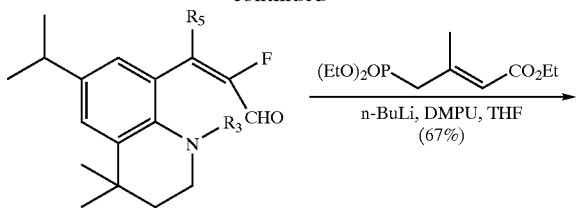

Intermediate 21 R₃ = Et, R₅ = Me
Intermediate 22 R₃ = Et, R₅ = Et
Intermediate 23 R₃ = n-Pr, R₅ = Me

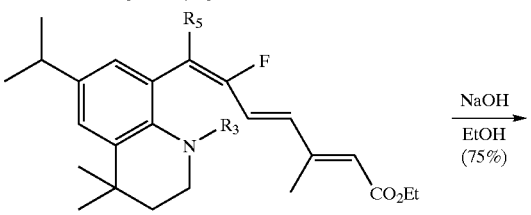

Intermediate 24 R₃ = Et, R₅ = Me
Intermediate 25 R₃ = Et, R₅ = Et
Intermediate 26 R₃ = n-Pr, R₅ = Me Experimental Procedures for Synthesizing the Exemplary Compounds of the Invention 3-Methyl-but-2-enoic acid (4-isopropyl-phenyl)-amide (Intermediate 1)

To a solution of 4-isopropylaniline (5.0 g, 37.0 mmol) in 100 ml of anhydrous $CH_2Cl_2$ under argon at 0° C. was added 3,3-dimethylacryloyl chloride (4.12 ml, 37.0 mmol). Pyridine (3.0 ml, 40.6 mmol) was added, and the mixture was stirred at 25° C. for 12 hours. The reaction was quenched with water and extracted with ethyl ether. The organic layer was washed with water, and brine, dried over $Na_2SO_4$ and were in vacuo to give the title compound as a light brown solid.

$^1$H NMR (300 MHz, $CDCl_3$): δ1.21 (s, 3H), 1.24 (s, 3H), 2.22 (s, 3H), 2.85 (s, 3H), 2.87 (m, 1H), 5.70 (s, 1H), 7.06 (s, NH), 7.17 (d, J=8.4 Hz, 2H), 7.44 (d, J=7.5 Hz, 2H).

6-Isopropyl-4,4-dimethyl-3,4-dihydro-1H-quinolin-2-one (Intermediate 2)

To a solution of 3-methyl-but-2-enoic acid (4-isopropyl-phenyl)-amide (Intermediate 1, 8.12 g, 37.4 mmol) in 100 ml of anhydrous $CH_2Cl_2$ under argon at 0° C. was slowly added aluninum chloride (20 g, 150 mmol) through a powder addition fumnel. The cooling bath was removed and the mixture was stirred at ambient temperature for 3 hours. The reaction was re-cooled to 0° C. and slowly quenched with ice. The product was extracted with diethyl ether. The organic layer was washed with water, saturated $NaHCO_3$ and brine, dried over $Na_2SO_4$, concentrated in vacuo and purified by column chromatography (silica, first using 25% ethyl acetate in hexane followed by 50% ethyl acetate in hexane) to give the title compound as a white solid.

$^1$H NMR (300 MHz, $CDCl_3$): δ1.23 (s, 3H), 1.26 (s, 3H), 1.34 (s, 6H), 2.48 (s, 3H), 2.91 (m, 1H), 6.67 (d, J=8.0 Hz, 2H), 7.05 (dd, J=1.9 Hz, J=6.1 Hz, 1H), 7.14 (s, 1H).

7-Bromo-6-isopropyl-4,4-dimethyl-3,4-dihydro-1H-quinolin-2-one ((Intermediate 3)

To a solution of 6-isopropyl-4,4-dimethyl-3,4-dihydro-1H-quinolin-2-one (Intermediate 2, 4.46 g, 20.7 mmol) in 30 ml of glacial acetic acid at 0° C. was added bromine (1.60 ml, 31.1 mmol). The reaction was warmed to 25° C. for 2 hours, and then it was quenched with saturated $Na_2S_2O_3$. The products were extracted with diethyl ether. The organic layer was washed with water, and brine, dried over $Na_2SO_4$, concentrated in vacuo and purified by column chromatography (silica, using 25% ethyl acetate in hexane) to give the title compound as a yellow oil.

$^1$H NMR (300 MHz, $CDCl_3$): δ1.23 (s, 3H), 1.25 (s, 3H), 1.33 (s, 6H), 2.48 (s, 2H), 2.85 (m, 1H), 7.09 (s, 1H), 7.26 (s, 1H), 7.90 (s, NH).

8-Bromo-6-isopropyl-4,4-dimethyl-1,2,3,4-tetrahydro-quinoline (Intermediate 4)

To a solution of 7-bromo-6-isopropyl-4,4-dimethyl-3,4-dihydro-1H-quinolin-2-one (Intermediate 3, 3.93 g, 13.3 mmol) in 50 ml of anhydrous THF under argon at 0° C. was added borane-methyl sulfide (1.53 ml, 15.3 mmol). The reaction was stirred at 0° C. for 15 minutes, and thereafter was heated to 60° C. for 12 hours. The solution was cooled to 25° C. and the reaction quenched with saturated $Na_2S_2O_3$. The resulting solution was stirred at 25° C. for 30 minutes before the products were extracted with ethyl ether. The organic layer was washed with water, and brine, dried over $Na_2SO_4$ concentrated in vacuo and purified by column chromatography (silica, first using 2% ethyl acetate in hexane then 5% ethyl acetate in hexane) to produce the title compound as a clear oil.

$^1$H NMR (300 MHz, $CDCl_3$): δ1.18 (s, 3H), 1.21 (s, 3H), 1.30 (s, 6H), 1.74 (t, J=5.8 Hz, 2H), 2.78 (m, 1H), 3.37 (t, J=5.8 Hz, 2H), 4.40 (s, NH), 7.00 (s, 1H), 7.12 (s, 1H).

8-Bromo-6-isopropyl-4,4-dimethyl-1-ethyl-1,2,3,4-tetrahydro-quinoline (Intermediate 5) General Procedure A To a solution of 8-bromo-6-isopropyl-4,4-dimethyl-1,2,3,4-tetrahydro-quinoline (Intermediate 4, 3.45 g, 10.5 mmol) in 25 mL of anhydrous dimethylacetamide under argon was added ethyl iodide (4.25 ml, 53 mmol) and potassium carbonate (7.24 g, 53 mmol). The reaction was heated to 70° C. for 60 hours. The reaction was cooled to 25° C. and extracted with diethyl ether. The organic layer was washed with water, and brine, dried over $Na_2SO_4$, concentrated in vacuo and purified by column chromatography (silica, using 5% ethyl acetate in hexane) to produce the title compound as a yellow oil.

$^1$H NMR (300 MHz, $CDCl_3$): δ1.25 (m, 3H), 1.26 (s, 3H), 1.27 (s, 3H), 1.29 (s, 6H), 1.65 (m, 2H), 2.80 (m, 1H), 2.95 (q, J=7.0 Hz, 2H), 3.07 (m, 1H), 7.09 (d, J=2.0 Hz, 1H), 7.25 (d, J=2.0 Hz, 1H).

8-Bromo-6-isopropyl-4,4-dimethyl-1-n-propyl-1,2,3,4-tetrahydro-quinoline (Intermediate 6)

Following General Procedure A, 8-bromo-6-isopropyl-4,4-dimethyl-1-alkyl-1,2,3,4-tetrahydro-quinoline (Intermediate 4, 3.0 g, 9.1 mmol) and 1-iodopropane (5.2 g, 46 mmol) were reacted to produce the title compound as a yellow oil.

$^1$H NMR (300 MHz, $CDCl_3$): δ0.94 (t, J=7.4 Hz, 3H), 1.19 (m, 3H), 1.21 (s, 3H), 1.28 (s, 6H), 1.63 (m, 2H), 1.80 (m, 2H), 2.80 (m, 1H), 2.90 (m, 2H), 3.10 (m, 2H), 7.08 (d, J=2.0 Hz, 1H), 7.25 (d, J=2.0 Hz, 1H).

6-Isopropyl-4,4-dimethyl-1-ethyl-1,2,3,4-tetrahydro-quinoline-8-carbaldehyde (Intermediate 7) General Procedure B To a solution of 8-bromo-6-isopropyl-4,4-dimethyl-1-ethyl-1,2,3,4-tetrahydro-quinoline (Intermediate 5, 6.81 g, 24.9 mmol), and 150 ml of anhydrous THF under argon at −78° C. was slowly added 1.6 M solution of n-butyl lithium and hexane (33 ml, 52.4 mmol). The reaction mixture was stirred at −78° C. for 10 minutes and thereafter N,N-cirmethylformamide (8.0 ml, 100 mmol) was added. The resulting reaction mixture was stirred at −78° C. for 15 minutes and then quenched with saturated $NH_4Cl$. The product was extracted with diethyl ether. The organic layer was washed with water and brine, dried over $Na_2SO_4$, concentrated in vacuo and purified by column chromatography (silica, using 5% ethyl acetate in hexane) to give the title compound as a yellow oil.

$^1$H NMR (300 MHz, CDCl$_3$): δ1.30 (m, 15H), 1.71 (m, 2H), 2.82 (m, 1H), 3.20 (m, 4H), 7.29 (d, J=2.0 Hz, 1H), 7.49 (d, J=2.1 Hz, 1H), 10.0 (s, 1H).

6-Isopropyl-4,4-dimethyl-1-n-propyl-1,2,3,4-tetrahydro-quinoline-8-carbaldehyde (Intermediate 8)

Following General Procedure B, 8-bromo-6-isopropyl-4,4-dimethyl-1-n-propyl-1,2,3,4-tetrahydro-quinoline (Intermediate 6, 5.64 g, 19.6 mmol) and N,N-dimethylformamide (6.0 g, 78.5 mmol) were reacted to produce the title compound as a yellow oil.

$^1$H NMR (300 MHz, CDCl$_3$): δ0.91 (t, J=7.4 Hz, 3H), 1.21 (s, 3H), 1.23 (s, 3H), 1.28 (m, 2H), 1.30 (s, 6H), 1.74 (m, 2H), 2.92 (m, 1H). 3.07 (m, 2H), 3.20 (m, 2H), 7.28 (d, J=2.0 Hz, 1H), 7.48 (d, J=2.0 Hz, 1H), 10.0 (s, 1H).

1-(1-Ethyl-6-isopropyl-4,4-dimethyl-1,2,3,4-tetrahydro-quinolin-8-yl-ethan-1-ol (Intermediate 9) General Procedure C To a solution of 6-isopropyl-4,4-dimethyl-1-ethyl-1,2,3,4-tetrahydro-quinoline-8-carbaldehyde (Intermediate 7, 2.00 g, 9.00 mmol) and 35 ml of anhydrous THF under argon at −78° C. was slowly added 3 M solution of methyl magnesium bromide in THF (7.5 ml, 22.5 mmol). The resulting solution was stirred at −78° C. for 45 minutes. The reaction was quenched with saturated NH$_4$Cl and the product was extracted with diethyl ether. The organic extract was washed with water, and brine, dried over Na$_2$SO$_4$ and concentrated in vacuo. The residue was purified by column chromatography using 5% ethyl acetate in hexane to yield the title compound as light yellow oil.

$^1$H NMR (300 MHz, CDCl$_3$): δ1.12 (t, J=7.3 Hz, 3H), 1.20 (s, 3H), 1.21 (s, 3H), 1.24 (s, 3H), 1.34 (s, 3H), 1.44 (m, 1H), 1.56 (m, 2H). 2.90 (m, 3H), 3.10 (m, 4H), 5.13(m, 1H), 6.10 (s, OH), 6.91 (d, J=2.0 Hz, 1H), 7.08 (d, J=2.0 Hz, 1H).

1-(1-Ethyl-6-isopropyl-4,4-dimethyl-1,2,3,4-tetrahydro-quinolin-8-yl)-propan-1-ol (Intermediate 10)

Following General Procedure C, 6-isopropyl-4,4-dimethyl-1-ethyl-1,2,3,4-tetrahydro-quinoline-8-carbaldehyde (Intermediate 7, 5.78 g, 26 mmol) and a solution of ethyl magnesium bromide (2M, 35 ml, 65 mmol) in THF were reacted to give the title compound as a yellow oil after purification by column chromatography using 5% ethyl acetate in hexane.

$^1$H NMR (300 MHz, CDCl$_3$): δ1.12 (t, J=7.3 Hz, 3H), 1.22 (s, 15H), 1.79 (m, 2H), 1.90 (m, 2H). 2.80 (m, 1H), 2.85 (m, 2H), 3.47 (m, 2H), 4.85 (m, 2H), 5.60 (s, OH), 6.97 (d, J=2.0 Hz, 1H), 7.06 (d, J=2.0 Hz, 1H).

1-(6-Isopropyl-4,4-dimethyl-1-n-propyl-1,2,3,4-tetrahydro-quinolin-8-yl)-ethanol (Intermediate 11)

Following General Procedure C, 6-isopropyl-4,4-dimethyl-1-n-propyl-1,2,3,4-tetrahydro-quinoline-8-carbaldehyde (Intermediate 8, 4.54 g, 19.2 mmol) and a solution of methyl magnesium bromide (3M, 16 ml, 47.9 mmol) in THF were reacted to give the title compound as a light yellow oil after purification by column chromatography using 5% ethyl acetate in hexane.

$^1$H NMR (300 MHz, CDCl$_3$): δ0.96 (t, J=7.3 Hz, 3H), 1.21 (s, 3H), 1.23 (s, 3H), 1.25 (s, 3H), 1.35 (s, 3H), 1.43 (m, 1H), 1.57 (m, 2H). 1.71 (m, 2H), 2.91 (m, 3H), 3.09 (m, 2H), 3.15 (m, 2H), 5.15 (m, 1H), 6.28 (s, OH), 6.90 (d, J=2.0 Hz, 1H), 7.08 (d, J=2.0 Hz, 1H).

1-(1-Ethyl-6-isopropyl-4,4-dimethyl-1,2,3,4-4-tetrahydro-quinolin-8-yl)-ethanone (Intermediate 12) General Procedure D To a solution of 1-(1-ethyl-6-isopropyl-4,4-dimethyl-1,2,3,4-tetrahydro-quinolin-8-yl)-ethan-1-ol (Intermediate 9, 1.50 g, 6.33 mmol) in 15 ml of CH$_2$Cl$_2$ at 0° C. was added 4-methylmorpholine N-oxide (1.48 g, 12.7 mmol), tetrapropylammonium perruthenate (333 mg, 0.95 mmol), and 4 Å molecular sieve powder (150 mg). The mixture was stirred at 0° C. and allowed to warm gradually while being monitored carefullly. As soon as the temperature rose to 25° C., the reaction was re-cooled in an ice bath. The crude mixture was immediately loaded onto a pre-packed silica gel column. The column was first eluted with 100% hexane, and then with 5% ethyl acetate and hexane to yield the title compound as a yellow oil.

$^1$H NMR (300 MHz, CDCl$_3$): δ1.10 (t, J=7.3 Hz, 3H), 1.20 (s, 3H), 1.21 (s, 3H), 1.29 (s, 6H), 1.70 (m, 2H), 2.56 (s, 3H), 2.80 (s, 1H), 3.00 (q, J=7.3 Hz, 2H), 3.20 (m, 2H), 7.04 (d, J=2.0 Hz, 1H), 7.07 (d, J=2.1 Hz, 1H).

1-(1-Ethyl-6-isopropyl-4,4-dimethyl-1,2,3,4-tetrahydro-quinolin-8-yl)-propan-1-one (Intermediate 13)

Following General Procedure D, 1-(1-ethyl-6-isopropyl-4,4-dimethyl-1,2,3,4-tetrahydro-quinolin-8-yl)-propan-1-ol (Intermediate 10, 5.37 g, 21.3 mmol) and 4-methylmorpholine N-oxide (5.00 g, 42.6 mmol) were reacted to give the title compound as a yellow oil.

$^1$H NMR (300 MHz, CDCl$_3$): δ1.07 (t, J=7.1 Hz, 3H), 1.14 (t, J=7.3 Hz, 3H), 1.20 (s, 3H), 1.21 (s, 3H), 1.29 (s, 6H), 1.68 (m, 2H), 2.81 (s, 1H), 2.92 (m, 4H), 3.17 (m, 2H), 6.93 (d, J=2.0 Hz, 1H), 7.15 (d, J=2.1 Hz, 1H).

1-(6-Isopropyl-4,4-dimethyl-1-n-propyl-1,2,3,4-tetrahydro-quinolin-8-yl)-ethanone (Intermediate 14)

Following General Procedure D, 1-(1-n-propyl-6-isopropyl-4,4-dimethyl-1,2,3,4-tetrahydro-quinolin-8-yl)-ethan-1-ol (Intermediate 11, 4.54 g, 18.1 mmol) and 4-methylmorpholine N-oxide (4.23 g, 36.2 mmol) were reacted to give the title compound as a yellow oil.

1H NMR (300 MHz, CDCl$_3$): δ0.80 (t, J=7.3 Hz, 3H), 1.20 (s, 3H), 1.21 (s, 3H), 1.30 (s, 6H), 1.60 (m, 2H), 1.71 (m, 2H), 2.59 (s, 3H), 2.81 (s, 1H), 2.90 (m, 2H), 3.20 (m, 2H), 7.05 (d, J=2.0 Hz, 1H), 7.18 (d, J=2.1 Hz, 1H).

(E)-3-(1-Ethyl-6-isopropyl-4,4-dimethyl-1,2,3,4-tetrahydro-quinolin-8-yl)-2-fluro-but-2-enoic acid ethyl ester (Intermediate 15) General Procedure E To a solution of a 1.6 M solution of n-butyl lithium in hexane (3.33 ml, 5.33 mmol) and 20 ml of anhydrous THF under argon at −78° C. was slowly added triethyl-2-fluoro-2-phosphonoacetate (1.29 g, 5.33 mmol). After 40 minutes at −78° C., a solution of 1-(1-ethyl-6-isopropyl-4,4-dimethyl-1,2,3,4-tetrahydro-quinolin-8-yl)-ethanone (Intermediate 12, 497 mg, 1.33 mmol) in 4 ml THF was added by cannula. The resulting mixture was stirred at −78° C. for 10 minutes, allowed to warm up to room temperature, and then heated to 80° C. for 12 hours. The reaction was quenched with saturated NH$_4$Cl and product was extracted with ethyl ether. The extract was washed with water, and brine, dried over Na$_2$SO$_4$, concentrated in vacuo, and the residue was purified by column chromatography using 2% ethyl acetate in hexane to yield the title compound as a yellow oil.

$^1$H NMR (300 MHz, CDCl$_3$): δ0.99 (t, J=7.1 Hz, 3H), 1.18 (t, J=7.0 Hz, 3H), 1.27 (s, 3H), 1.29 (s, 3H), 1.30 (s, 3H), 1.31 (s, 3H), 1.79 (m, 2H), 2.15 (d, J=4.4 Hz, 3H), 2.79 (m, 3H), 3.00 (m, 2H), 4.04 (q, J=7.0 Hz, 2H), 6.63 (d, J=2.0 Hz, 1H), 7.06 (d, J=2.0 Hz, 1H).

(E)-3-(1-Ethyl-6-isopropyl-4,4-dimethyl-1,2,3,4-tetrahydro-quinolin-8-yl)-2-fluro-pent-2-enoic acid ethyl ester (Intermediate 16)

Following General Procedure E, triethyl-2-fluoro-2-phosphonoacetate (15.1 g, 62.3 mmol) and 1-(1-ethyl-6-isopropyl-4,4-dimethyl-1,2,3,4-tetrahydro-quinolin-8-yl)-1- propanone (Intermediate 13, 4.48 g, 15.6 mmol) were reacted to give the title compound as bright yellow oil after purification by flash chromatography (SiO$_2$, 2:98 ethyl acetate:hexane).

$^1$H NMR (300 MHz, CDCl$_3$): δ0.92 (t, J=7.6 Hz, 3H), 0.98 (t, J=7.0 Hz, 3H), 1.09 (t, J=7.0 Hz, 3H), 1.17 (s, 3H), 1.19 (s, 3H), 1.27 (s, 3H), 1.30 (s, 3H), 1.65 (m, 2H), 2.00 (m, 2H), 2.80 (m, 1H), 2.97 (m, 4H), 4.00 (q, J=7.0 Hz, 2H), 6.57 (d, J=2.0 Hz, 1H), 7.06 (d, J=2.0 Hz, 1H).

(E)-2-Fluoro-3-(6-isopropyl-4,4-dimethyl-1-n-propyl-1,2,3,4-tetrahydro-quinolin-8-yl)-but-2-enoic acid ethyl ester (Intermediate 17)

Following General Procedure E, triethyl-2-fluoro-2-phosphonoacetate (8.36 g, 34.5 mmol) and 1-(1-n-propyl-6-isopropyl-4,4-dimethyl-1,2,3,4-tetrahydro-quinolin-8-yl)-ethanone (Intermediate 14, 2.78 g, 9.86 mmol) were reacted to give the title compound as a yellow oil after purification by flash chromatography (SiO$_2$, 2:98 ethyl acetate:hexane).

$^1$H NMR (300 MHz, CDCl$_3$): δ0.97 (t, J=7.0 Hz, 3H), 1.18 (s, 3H), 1.20 (s, 3H), 1.27 (s, 3H), 1.30 (s, 3H), 1.50 (m, 5H), 1.79 (m, 2H), 2.14 (d, J=4.4 Hz, 3H), 2.79 (m, 3H), 3.00 (m, 2H), 4.03 (q, J=7.0 Hz, 2H), 6.64 (d, J=2.0 Hz, 1H), 7.07 (d, J=2.0 Hz, 1H).

(E)-3-(1-Ethyl-6-isopropyl-4,4-dimethyl-1,2,3,4-tetrahydro-quinolin-8-2-fluoro-but-2-en-1-ol (Intermediate 18) General Procedure F To a solution of (E)-3-(1-ethyl-6-isopropyl-4,4-dimethyl-1,2,3,4-tetrahydro-quinolin-8-yl)-2-fluoro-but-2-enoic acid ethyl ester (Intermediate 15, 199 mg, 0.55 mmol) in 10 ml of anhydrous THF under argon at 0° C. was added a 1.0 M solution of diisobutylaluminum hydride (2.20 ml, 2.20 mmol) in hexanes. The resulting mixture was stirred at 0° C. to 25° C. for 1 h. The reaction was cooled to 0 ° C. and quenched slowly with saturated NH$_4$Cl (0.5 ml), Celite (200 mg), and diluted with diethyl ether (10 ml). The resulting mixture was stirred at 25 ° C. for 1 hour. The product was filtered through a pad of Celite. The solution was dried over Na$_2$SO$_4$ and concentrated in vacuo. The residue was purified by column chromatography using ethyl acetate: hexane (1:4) to yield the title compound as a yellow oil.

$^1$H NMR (300 MHz, CDCl$_3$): δ1.15 (t, J=7.3 Hz, 3H), 1.20 (s, 3H), 1.22 (s, 3H), 1.30 (s, 3H), 1.33 (s, 3H), 1.44 (m, 1H), 1.82 (m, 1H), 2.05 (d, J=3.4 Hz, 3H), 2.80 (m, 2H), 2.90 (m, 1H), 3.05 (m, 2H), 3.85 (m, 2H), 4.80 (s, OH), 6.76 (d, J=2.0 Hz, 1H), 7.08 (d, J=2.0 Hz, 1H).

(E)-3-(1-Ethyl-6-isopropyl-4,4-dimethyl-1,2,3,4-tetrahydro-quinolin-8-yl)-2-fluoro-pent-2-en-1-ol (Intermediate 19)

Following General Procedure F, (E)-3-(1-ethyl-6-isopropyl-4,4-dimethyl-1,2,3,4-tetrahydro-quinolin-8-yl)-2-fluoro-pent-2-enoic acid ethyl ester (Intermediate 16, 2.37 g, 9.08 mmol) and a 1 M solution of diisobutylalluminum hydride in hexanes (36.3 ml, 36.3 mmol) were reacted to give the title compound as light yellow oil after purification by flash chromatography (SiO$_2$, first eluted with 5:95 ethyl acetate:hexane, followed by 1:9 ethyl acetate:hexane).

$^1$H NMR (300 MHz, CDCl$_3$): δ0.96 (t, J=7.5 Hz, 3H), 1.16 (t, J=7.3 Hz, 3H), 1.20 (s, 3H), 1.22 (s, 3H), 1.29 (s, 3H), 1.32 (s, 3H), 1.80 (m, 2H), 2.20 (m, 2H), 2.80 (m, 1H), 2.90 (m, 4H), 3.90 (m, 2H), 6.80 (d, J=2.0 Hz, 1H), 7.08 (d, J=2.0 Hz, 1H).

(E)-2-Fluoro-3-(6-isopropyl-4,4-dimethyl-1-n-propyl-1,2,3,4-tetrahydro-quinolin-8-yl)-but-2-en-1-ol (Intermediate 20)

Following General Procedure F, (E)-3-(1-n-propyl-6-isopropyl-4,4-dimethyl-1,2,3,4-tetrahydro-quinolin-8-yl)-2-fluoro-but-2-enoic acid ethyl ester (Intermediate 17, 1.43 g, 3.82 mmol) and a 1 M solution of diisobutylalluminum hydride in hexanes (15.3 ml, 15.3 mmol) were reacted to give the title compound as a light yellow oil after purification by flash chromatography (SiO$_2$, first eluted with 5:95 ethyl acetate:hexane, followed by 1:9 ethyl acetate:hexane).

$^1$H NMR (300 MHz, CDCl$_3$): δ0.87 (t, J=7.0 Hz, 3H), 1.20 (s, 3H), 1.22 (s, 3H), 1.28 (s, 2H), 1.29 (s, 3H), 1.33 (s, 3H), 1.60 (m, 2H), 2.04 (m, 3H), 2.80 (m, 2H), 3.12 (m, 2H), 3.80 (m, 2H), 6.76 (d, J=2.0 Hz, 1H), 7.07 (d, J=2.0 Hz, 1H).

(E)-3-(1-Ethyl-6-isopropyl-4,4-dimethyl-1,2,3,4-tetrahydro-quinolin-8-yl)-2-fluoro-but-2-enal (Intermediate 21) General Procedure G To a solution of (E)-3-(1-ethyl-6-isopropyl-4,4-dimethyl-1,2,3,4-tetrahydro-quinolin-8-yl)-2-fluoro-but-2-en-1-ol (Intermediate 18, 133 mg, 0.35 mmol) in 2 ml of CH$_2$Cl$_2$ at 0° C. was added 4-methylmorpholine N-oxide (83 mg, 0.71 mmol), tetrapropylammonium perruthenate (18.6 mg, 0.05 mmol), and 4 Å molecular sieve powder (10 mg). The mixture was stirred at 0° C. for 5 min, and the bath was removed. The temperature of reaction mixture was monitored carefully, and as soon as the temperature rose to 25° C., the reaction was re-cooled in an ice bath. The cooled reaction mixture was loaded onto a pre-packed silica gel column, and the product was eluted with 100% hexane followed by 2% ethyl acetate in hexane to yield the title compound as a bright yellow solid.

$^1$H NMR (300 MHz, CDCl$_3$): δ1.02 (t, J=7.3 Hz, 3H), 1.20 (s, 3H), 1.22 (s, 3H), 1.30 (s, 6H), 1.60 (m, 2H), 2.27 (d, J=3.4 Hz, 3H), 2.80 (m, 1H), 2.85 (m, 2H), 3.06 (m, 2H), 6.78 (d, J=2.0 Hz, 1H), 7.15 (d, J=2.0 Hz, 1H), 9.24 (d, J=20 Hz, 1H).

(E)-3-(1-Ethyl-6-isopropyl-4,4-dimethyl-1,2,3,4-tetrahydro-quinolin-8-yl)-2-fluoro-pent-2-enal (Intermediate 22)

Following General Procedure G, (E)-3-(1-ethyl-6-isopropyl-4,4-dimethyl-1,2,3,4-tetrahydro-quinolin-8-yl)-2-fluoro-pent-2-en-1-ol (Intermediate 19, 2.45 g, 6.28 mmol) and N-methylmorpholine N-oxide (1.73 g, 12.6 mmol) were reacted to give the title compound as a bright yellow oil.

$^1$H NMR (300 MHz, CDCl$_3$): δ0.99 (t, J=7.3 Hz, 3H), 1.01 (t, J=7.0 Hz, 3H), 1.20 (s, 3H), 1.22 (s, 3H), 1.30 (s, 3H), 1.31 (s, 3H), 1.60 (m, 2H), 2.60 (m, 1H), 2.80 (m, 2H), 2.90 (m, 2H), 3.03 (m, 2H), 6.73 (d, J=2.0 Hz, 1H), 7.16 (d, J=2.0 Hz, 1H), 9.30 (d, J=20 Hz, 1H).

(E)-2-Fluoro-3-(6-isopropyl-4,4-dimethyl-1-n-propyl-1,2,3,4-tetrahydro-quinolin-8-yl)-but-2-enal (Intermediate 23)

Following General Procedure G, (E)-3-(1-n-propyl-6-isopropyl-4,4-dimethyl-1,2,3,4-tetrahydro-quinolin-8-yl)-2-fluoro-but-2-en-1-ol (Intermediate 20, 1.34 g, 4.04 mmol) and N-methylmorpholine N-oxide (947 mg, 8.08 mmol) were reacted to give the title compound as a bright yellow oil.

$^1$H NMR (300 MHz, CDCl$_3$): δ0.79 (t, J=7.3 Hz, 3H), 1.20 (s, 3H), 1.22 (s, 3H), 1.30 (s, 6H), 1.42 (m, 2H), 1.64 (m, 2H), 2.26 (d, J=4.1 Hz, 3H), 2.76 (m, 3H), 3.06 (m, 2H), 6.78 (d, J=2.0 Hz, 1H), 7.15 (d, J=2.0 Hz, 1H), 9.25 (d, J=20 Hz, 1H).

(2E,4E,6E)-7-(1-Ethyl-6-isopropyl-4,4-dimethyl-1,2,3 4-tetrahydro-quinolin-8-yl)-6-fluoro-3-methyl-octa-2,4,6-trienoic acid ethyl ester (Compound 24) General Procedure H To a solution of ethyl 4-(diethoxyphosphoryl)-3-methyl-but-2-enoate (210 mg, 0.80 mmol), 10 ml of anhydrous THF, and 1,3-dimethyl-3,4,5,6-tetrahydro-2(1H)-pyrimidinone (0.12 ml) under argon at −78° C. was slowly added a 1.6 M solution of n-butyl lithium and hexane (0.52 ml, 0.84 mmol). The resulting mixture was stirred at −78° C. for 30 minutes before a solution of (E)-3-(1-ethyl-6-isopropyl-4,4- dimethyl-1,2,3,4-tetrahydro-quinolin-8-yl)-2-fluoro-but-2-enal (Intermediate 21, 87 mg, 0.27 mmol) and 3 ml THF was added by cannula. The resulting mixture was stirred at 0° C. for 1 h. The reaction was quenched with saturated NH$_4$Cl, and the product was extracted with ethyl ether. The extract was washed with water, and brine, and dried over Na$_2$SO$_4$. The solution was filtered and concentrated in vacuo. The residue was purified by column chromatography using 5% ethyl acetate in hexane to yield the title compound as a bright yellow oil.

$^1$H NMR (300 MHz, CDCl$_3$): δ1.00 (t, J=7.0 Hz, 3H), 1.20 (s, 3H), 1.22 (s, 3H), 1.25 (m, 3H), 1.27 (s, 3H), 1.29 (s, 3H), 1.55 (m, 1H), 1.70 (m,1H), 2.14 (m, 6H), 2.80 (m, 2H), 2.90 (m, 1H), 3.07 (m, 2H), 4.14 (q, J=7.0 Hz, 2H), 5.84 (s, 1H), 6.50 (m, 3H), 6.71 (d, J=2.0 Hz, 1H), 7.08 (d, J=2.0 Hz, 1H).

(2E,4E,6E)-7-(1-Ethyl-6-isopropyl-4,4-dimethyl-1,2,3,4-tetrahydro-quinolin-8-yl)-6-fluoro-3-methyl-nona-2,4,6-trienoic acid ethyl ester (Compound 25)

Following General Procedure H, 4-(diethoxyphosphoryl)-3-methyl-but-2-enoate (2.18 g, 8.25 mmol) and (E)-3-(1-ethyl-6-isopropyl-4,4-dimethyl-1,2,3,4-tetrahydro-quinolin-8-yl)-2-fluoro-pent-2-enal (Intermediate 22, 936 mg, 2.84 mmol) were reacted to give the title compound as a bright yellow oil after purification by column chromatography using 2% ethyl acetate in hexane.

$^1$H NMR (300 MHz, CDCl$_3$): δ0.90 (t, J=7.0 Hz, 3H), 0.98 (t, J=7.0 Hz, 3H), 1.20 (s, 3H), 1.25 (m, 3H), 1.29 (s, 3H), 1.55 (m, 4H), 2.08 (m, 4H), 3.05 (m, 1H), 4.15 (q, J=7.0 Hz, 2H), 5.85 (s, 1H), 6.50 (m, 2H), 6.65 (d, J=2.0 Hz, 1H), 7.07 (d, J=2.0 Hz, 1H).

(2E,4E,6E)-6-Fluoro-7-(6-isopropyl-4,4-dimethyl-1-n-propyl-1,2,3,4-tetrahydro-quinolin-8-yl)-3-methyl-octa-2,4,6-trienoic acid ethyl ester (Compound 26)

Following General Procedure H, 4-(diethoxyphosphoryl)-3-methyl-but-2-enoate (2.03 g, 7.69 mmol) and (E)-3-(1-n-propyl-6-isopropyl-4,4-dimethyl-1,2,3,4-tetrahydro-quinolin-8-yl)-2-fluoro-pent-2-enal (Intermediate 23, 872 mg, 2.65 mmol) were reacted to give the title compound as a bright yellow oil after purification by column chromatography using 2% ethyl acetate in hexane.

$^1$H NMR (300 MHz, CDCl$_3$): δ0.76 (t, J=7.3 Hz, 3H), 1.20 (s, 3H), 1.22 (s, 3H), 1.24 (m, 3H), 1.29 (s, 3H), 1.32 (s, 3H), 1.50 (m, 2H), 1.75 (m, 2H), 2.11 (d, J=3.5 Hz, 3H), 2.20 (s, 3H), 2.65 (m, 1H), 2.80 (m, 2H), 3.10 (m, 2H), 4.14 (q, J=7.0 Hz, 2H), 5.85 (s, 1H), 6.50(m, 2H), 6.70 (d, J=2.0 Hz, 1H), 7.08 (d, J=2.0 Hz, 1H).

(2E,4E,6E)-7-(1-Ethyl-6-isopropyl-4,4-dimethyl-1,2,3,4-tetrahydro-quinolin-8-yl)-6-fluoro-3-methyl-octa-2,4,6-trienoic acid (Compound 27) General Procedure I To a solution of (2E,4E,6E)-7-(1-ethyl-6-isopropyl-4,4-dimethyl-1,2,3,4-tetrahydro-quinolin-8-yl)-6-fluoro-3-methyl-octa-2,4,6-trienoic acid ethyl ester (Compound 24, 117 mg, 2.74 mmol) and 5 ml of ethanol and 1 ml of THF was added 2 ml of 1 M NaOH(aq). The reaction was heated to 50° C. for 4 hours. The excess alcohol was removed by evaporation. The residue was neutralized with saturated NH$_4$Cl to pH=7 then extracted with ethyl acetate (3×10 ml). The combined organic layers were washed with water, and brine, dried over Na$_2$SO$_4$ and concentrated to give the crude acid as a residue. This was purified by column chromatography (silica, first using 100% hexane, followed by 5:95 ethyl acetate:hexane, then 1:1 ethyl acetate:hexane) to yield a yellow oil. The resulting yellow oil was recrystallized from acetonitrile to produce the title compound as a yellow solid.

$^1$H NMR (300 MHz, CDCl$_3$): δ1.00 (t, J=7.0 Hz, 3H), 1.20 (s, 3H), 1.22 (s, 3H), 1.30 (s, 3H), 1.33 (s, 3H), 1.55 (m, 1H), 1.75 (m, 1H), 2.14 (m, 6H), 2.80 (m, 2H), 2.90 (m, 1H), 3.07 (m, 2H), 5.86 (s, 1H), 6.48 (d, J=5.6 Hz, 1H), 6.52 (d, J=4.1 Hz, 1H), 6.71 (d, J=2.0 Hz, 1H), 7.08 (d, J=2.0 Hz, 1H).

(2E,4E,6E)-7-(1-Ethyl-6-isopropyl-4,4-dimethyl-1,2,3,4-tetrahydro-quinolin-8-yl)-6-fluoro-3-methyl-nona-2,4,6-trienoic acid (Compound 28)

Following General Procedure I, (2E,4E,6E)-7-(1-ethyl-6-isopropyl-4,4-dimethyl-1,2,3,4-tetrahydro-quinolin-8-yl)-6-fluoro-3-methyl-nona-2,4,6-trienoic acid ethyl ester (Compound 25, 630 mg, 14.3 mmol) was hydrolyzed with NaOH to yield the title compound as a yellow solid after purification by column chromatography (silica, first using 100% hexane, followed by 5:95 ethyl acetate:hexane, then 1:1 ethyl acetate:hexane) to yield a yellow oil. The resulting yellow oil was recrystallized from acetonitrile.

$^1$H NMR (300 MHz, CDCl$_3$): δ0.90 (t, J=7.0 Hz, 3H), 0.99 (t, J=7.0 Hz, 3H), 1.20 (s, 3H), 1.30 (s, 3H), 1.55 (m, 4H), 2.08 (s, 3H), 2.80 (m, 4H), 3.05 (m, 1H), 5.87 (s, 1H), 6.75 (m, 2H), 6.65 (d, J=2.0 Hz, 1H), 7.07 (d, J=2.0 Hz, 1H).

(2E,4E,6E)-6-Fluoro-7-(6-isopropyl-4,4-dimethyl-1-propyl-1,2,3,4-tetrahydro-quinolin-8-yl)-3-methyl-octa-2,4,6-trienoic acid (Compound 29)

Following General Procedure I, (2E,4E,6E)-7-(1-n-propyl-6-isopropyl-4,4-dimethyl-1,2,3,4-tetrahydro-quinolin-8-yl)-6-fluoro-3-methyl-octa-2,4,6-trienoic acid ethyl ester (Compound 26, 830 mg, 1.88 mmol) was hydrolyzed with NaOH to yield the title compound as a yellow solid after purification by column chromatography (silica, first using 100% hexane, followed by 5:95 ethyl acetate:hexane, then 1:1 ethyl acetate:hexane) to yield a yellow oil. The resulting yellow oil was recrystallized from acetonitrile.

$^1$H NMR (300 MHz, CDCl$_3$): δ0.75 (t, J=7.3 Hz, 3H), 1.20 (s, 3H), 1.22 (s, 3H), 1.29 (s, 3H), 1.32 (s, 3H), 1.55 (m, 4H), 2.11 (d, J=3.5 Hz, 3H), 2.20 (s, 3H), 2.65 (m, 1H), 2.80 (m, 2H), 3.10 (m, 2H), 5.87 (s, 1H), 6.48 (d, J=5.9 Hz, 1H), 6.52 (d, J=3.8 Hz, 1H), 6.70 (d, J=2.0 Hz, 1H), 7.07 (d, J=2.0 Hz, 1H).

Bilogical Activity, Modes of Adminstration

It has been discovered in accordance with the present invention that compounds of this invention are capable of significantly reducing serum glucose levels and reducing or maintaining serum triglyceride levels in diabetic mammals, without the undesirable side effects of reducing serum thyroxine levels (hypothyroidism) and transiently raising triglyceride levels (hypertriglyceridemia). The compounds of the invention are partial agonists of the RXRs. Table 1 below discloses the results of certain assays where the compounds of the invention were tested as agonists of RAR and RXR retinoid receptors.

One such assay is a chimeric receptor transactivation assay which tests for agonist-like activity in the RAR$_\alpha$, RAR$_\beta$ and RAR$_\gamma$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO093/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of the ligand binding assay are expressed in $K_i$ numbers. (See Cheng et al Biochemical Pharmacology Vol. 22 pp 3099–3108, expressly incorporated herein by reference.)

Efficacy in a transactivation assay is expressed as a percentage of the maximum potency attained by the compound compared to a standard which, in this case, is the compound named (2E,4E,1'S, 2'S)-3-methyl-5-[2'-methyl-2'-(5,5,8,8-tetramethyl-5,6,7,8-tetrahydro-naphthalen-2-yl)-cyclopropyl]-penta-2,4-dienoic acid. This standard compound is described in U.S. Pat. No. 6,114,533.

Table 1 discloses the activity of certain exemplary compounds of the invention in the above-described receptor transactivation and binding assays. Particularly, the transactivation data pertaining to activation of the RAR receptors were obtained in the chimeric assay, and the transactivation data pertaining to the activation of RXR receptors were obtained in the holoreceptor assay. In the chimeric receptor transactivation assay the compounds were essentially inactive in activating $RAR_\alpha$, $RAR_\beta$ and $RAR_\gamma$ receptors.

Table 1, NA stands for not active at all as an agonist and ND stands for not determined. The first row of numbers pertaining to each compound is the measured $EC_{50}$ number. The second row of numbers indicates efficacy as a percentage compared to the standard compound, (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid . The third row of numbers pertaining to each compound is the binding $K_i$ number.

An assay described below tests the effect of compounds of the invention on serum glucose, tryglyceride and thyroxine levels in female 9–10 weeks old db/db mice.

Description of Assay.

Female diabetic db/db (9–10 weeks old) mice were maintained on standard laboratory food and treated by oral gavage with vehicle (corn oil), standard compound (2E,4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid (5 mg/kg) or the test compound (5–100 mg/kg, as described in Table 2) daily for seven days at 8:00 AM. Blood samples (70 µl) were taken by orbital bleeding at 11:00 AM on day 0 (pre-treatment), day 3, and day 6. On day 7, a blood sample (700 µl) was taken at 11:00 AM and the animals were sacrificed. Glucose, triglyceride and thyroxine (T4) levels were determined on a Boehringer Manheim Hatachi Clinical Chemistry Analyzer using standard protocols provided by the manufacturer and reagents that were

TABLE 1

| compound | | RAR Trans. $EC_{50}$ nM RAR Bind. $K_i$ nM | | | RXR Trans. $EC_{50}$ nM RXR Bind. $K_i$ nM | | |
|---|---|---|---|---|---|---|---|
| Number | Structure | α | β | γ | α | β | γ |
| 29 | (structure) | NA | NA | NA | 2 (32) | 6 (27) | 2 (10) |
| | | 480 | 450 | 1.4k | 1 | 15 | ND |
| 27 | (structure) | NA | NA | NA | 0.1 (74) | 0.5 (77) | 0.1 (75) |
| | | 680 | 840 | 2.5k | 1 | 11 | ND |
| 28 | (structure) | NA | NA | NA | 0.3 (86) | 0.4 (66) | 0.3 (75) |
| | | 705 | 430 | 2.0k | 2 | 21 | 21 | supplied in commercially available kits (glucose and T4: Boehringer Manheim; triglycerides: Roche Diagnostics). A NUMBER OF animals were treated in each group. The results of the assays are summarized in Table 2.

| Treatment (dose) | Glucose (mg/dl) | | | Triglycerides (mg/dl) | | T4 (µg/dL) |
| --- | --- | --- | --- | --- | --- | --- |
| | Day 0 | Day 3, 3h | Day 6, 3h | Day 0 | Day 3, 3h | Day 7 |
| Vehicle (Corn oil) | 549 ± 121 | 531 ± 133 | 535 ± 177 | 306 ± 143 | 265 ± 140 | 2.3 ± 0.6 |
| Standard compound (4 mg/kg) | 524 ± 45 | 512 ± 156 | 459 ± 148 | 273 ± 66 | 755 ± 464 | 1.4 ± 0.5 |
| Compound 29 (50 mg/kg) | 523 ± 84 | 476 ± 96 | 441 ± 184 | 316 ± 339 | 326 ± 111 | 2.3 ± 0.5 |

As the data indicate, the compounds of the invention not only cause significant decrease in serum glucose levels and maintain or reduce triglyceride levels in diabetic mammals, but in contrast with the prior art standard compound (2E, 4E,1'S,2'S)-3-methyl-5-[2'-methyl-2'-(5,5,8,8-tetramethyl-5,6,7,8-tetrahydro-naphthalen-2-yl)-cyclopropyl]-penta-2,4-dienoic acid do not have the undesirable side effect of reducing serum thyroxine levels.

Modes of Administration, Dosing

To treat diabetic mammals, including humans for the purpose of reducing serum glucose levels in said mammals a pharmaceutical composition containing one or more compound of the invention is administered to the mammal in daily doses in the range of 1 to 100 mg per kg body weight of the mammal. Preferably the daily dose is between 10 to 50 mg per kg body weight of the mammal.

Generally speaking the compounds of the invention are also useful for preventing or treating diseases and conditions that are responsive to compounds that promote the expression of or bind to receptors belonging to the steroid or thyroid receptor superfamily. More specifically the compounds of the invention can be used for preventing or treating skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (OVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

To treat diabetes the compounds of this invention are preferably administered, orally.

For the prevention or treatment of other diseases or conditions the compounds of the invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 1 and 50 mg per kg of body weight per day would be expected to effect a therapeutic result in the treatment of many diseases for which these compounds are useful.

What is claimed is:

1. A compound of the formula

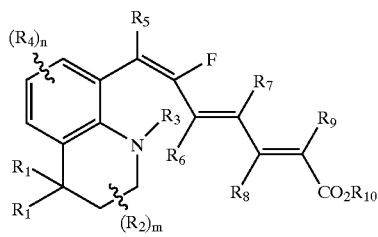

where m is an integer having the values of 0 to 4;
n is an integer having the values of 0 to 3;
$R_1$ is independently H, or alkyl of 1 to 6 carbons;
$R_2$ is independently H, alkyl of 1 to 6 carbons, F, Cl, Br or I;
$R_3$ is alkyl of 1 to 6 carbons;
$R_4$ is independently H, alkyl of 1 to 6 carbons, F, Cl, Br or I;
$R_5$ is alkyl of 1 to 6 carbons;
$R_6$, $R_7$, $R_8$ and $R_9$ are independently, H, alkyl of 1 to 3 carbons, Cl or F;
$R_{10}$ is H, alkyl of 1 to 6 carbons, or methoxymethyl, or a pharmaceutically acceptable salt of said compound.

2. A compound in accordance with claim 1 where $R_1$ is alkyl of 1 to 3 carbons.

3. A compound in accordance with claim 1 where $R_3$ is alkyl of 1 to 3 carbons.

4. A compound in accordance with claim 1 where $R_4$ is alkyl of 1 to 4 carbons.

5. A compound in accordance with claim 1 where $R_4$ is branch-chained alkyl.

6. A compound in accordance with claim 1 where $R_5$ is alkyl of 1 to 3 carbons.

7. A compound in accordance with claim 1 where $R_8$ is methyl.

8. A compound in accordance with claim 1 where $R_6$, $R_7$ and $R_9$ are H.

9. A compound of the formula

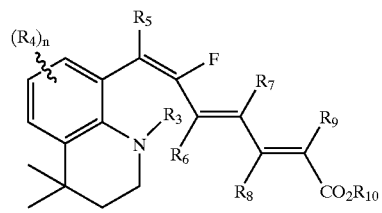

where n is an integer having the values of 0 to 3;
$R_3$ is alkyl of 1 to 6 carbons;
$R_4$ is independently alkyl of 1 to 6 carbons;
$R_5$ is alkyl of 1 to 3 carbons;
$R_6$, $R_7$, $R_8$ and $R_9$ are independently, H, alkyl of 1 to 3 carbons, Cl or F;
$R_{10}$ is H, alkyl of 1 to 6 carbons, or methoxymethyl, or a pharmaceutically acceptable salt of said compound.

10. A compound in accordance with claim 9 where n is 1.

11. A compound in accordance with claim 10 where $R_3$ is alkyl of 1 to 3 carbons.

12. A compound in accordance with claim 11 where $R_4$ is branch-chained alkyl.

13. A compound in accordance with claim 12 where $R_4$ is iso-propyl.

14. A compound of the formula

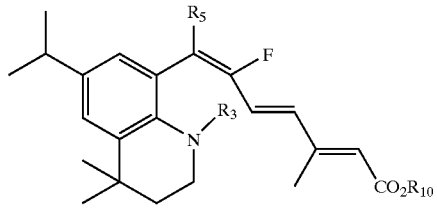

where $R_3$ is alkyl of 1 to 6 carbons;
$R_5$ is alkyl of 1 to 3 carbons, and
$R_{10}$ is H, alkyl of 1 to 6 carbons, or methoxymethyl, or a pharmaceutically acceptable salt of said compound.

15. A compound in accordance with claim 14 where $R_3$ is ethyl.

16. A compound in accordance with claim 15 where $R_5$ is methyl.

17. A compound in accordance with claim 16 where $R_{10}$ is H, ethyl or a pharmaceutically acceptable salt of said compound.

18. A compound in accordance with claim 15 where $R_5$ ethyl.

19. A compound in accordance with claim 18 where $R_{10}$ is H, ethyl or a pharmaceutically acceptable salt of said compound.

20. A compound in accordance with claim 14 where $R_3$ is n-propyl.

21. A compound in accordance with claim 20 where $R_5$ is methyl.

22. A compound in accordance with claim 21 where $R_{10}$ is H, ethyl or a pharmaceutically acceptable salt of said compound.

23. A process for reducing the serum glucose level of a mammal comprising administering to the mammal in need thereof an effective amount amount a compound of the formula

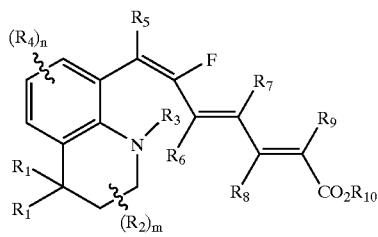

where m is an integer having the values of 0 to 4;

n is an integer having the values of 0 to 3;

$R_1$ is independently H, or alkyl of 1 to 6 carbons;

$R_2$ is independently H, alkyl of 1 to 6 carbons, F, Cl, Br or I;

$R_3$ is alkyl of 1 to 6 carbons;

$R_4$ is independently H, alkyl of 1 to 6 carbons, F, Cl, Br or I;

$R_5$ is alkyl of 1 to 6 carbons;

$R_6$, $R_7$, $R_8$ and $R_9$ are independently, H, alkyl of 1 to 3 carbons, Cl or F;

$R_{10}$ is H, alkyl of 1 to 6 carbons, or methoxymethyl, or a pharmaceutically acceptable salt of said compound.

24. A process in accordance with claim 23 where the compound used in the process is in accordance with the formula

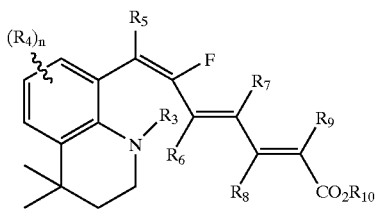

where $R_4$ is independently alkyl of 1 to 6 carbons;

$R_5$ is alkyl of 1 to 3 carbons.

25. A process in accordance with claim 23 where the compound used in the process is in accordance with the formula

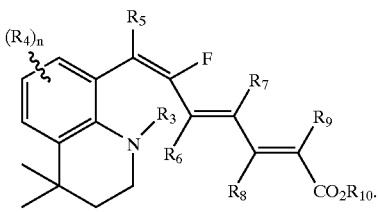

* * * * *

UNITED STATES PATENT AND TRADEMARK OFFICE
CERTIFICATE OF CORRECTION

PATENT NO. : 6,734,193 B1
DATED : May 11, 2004
INVENTOR(S) : Duong et al.

It is certified that error appears in the above-identified patent and that said Letters Patent is hereby corrected as shown below:

Column 3
Line 13, "Some of the compounds of the" should be deleted and inserted in line 14 as a new paragraph.

Column 9,
Line 47, "fumnel." should be -- funnel --

Column 10,
Line 63, "cirmethylformamide" should be -- dimethylformamide --

Column 19,
Line 63, "(OVR)" should be -- (PVR) --

Column 24,
Lines 18-28, " 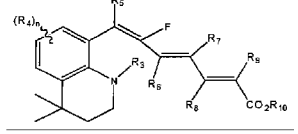 " should be -- 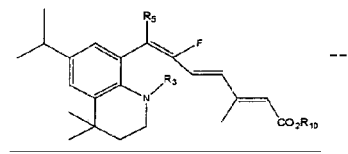 --

Signed and Sealed this

Thirtieth Day of November, 2004

JON W. DUDAS
*Director of the United States Patent and Trademark Office*